US00PP36293P2

(12) United States Plant Patent
Rimland

(10) Patent No.: US PP36,293 P2
(45) Date of Patent: Dec. 3, 2024

(54) ***EPIPREMNUM* PLANT NAMED 'CF-MKR-EA1'**

(50) Latin Name: *Epipremnum aureum*
Varietal Denomination: CF-MKR-EA1

(71) Applicant: Michael Kerry Rimland, Miami, FL (US)

(72) Inventor: Michael Kerry Rimland, Miami, FL (US)

(73) Assignee: Hiroaki Asaoka, Anjo (JP)

( * ) Notice: Subject to any disclaimer, the term of this patent is extended or adjusted under 35 U.S.C. 154(b) by 0 days.

(21) Appl. No.: 18/445,822

(22) Filed: Feb. 21, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct *Epipremnum aureum* plant named 'CF-MKR-EA1' which is characterized by a trailing and vining habit, with glossy cordate foliage that emerges with a vibrant yellow coloration and matures to dark green, as well as the stability of these characteristics from generation to generation.

3 Drawing Sheets

Latin name of the genus and species: The Latin name of the genus and species of the novel variety disclosed herein is *Epipremnum aureum.*

Variety denomination: The inventive variety of *Epipremnum* disclosed herein has been given the variety denomination 'CF-MKR-EA1'.

BACKGROUND OF THE INVENTION

Parentage: 'CF-MKR-EA1' is a spontaneous partial-plant branch mutation which was discovered growing amongst a cultivated population of *Epipremnum aureum* 'Lemon Meringue' plants (U.S. Pat. No. 34,521). The claimed plant was discovered by the inventor in October of 2022 at a commercial greenhouse near Miami, Florida and was first noted for the bright yellow coloration of the juvenile foliage that contrasted with the dark green mature foliage. At that time, stem cuttings were harvested from the mutated branch, rooted, and the resulting plants grown to maturity in order to confirm the distinguishing characteristics first observed and the stability thereof. The new plant was selected for commercialization in March of 2023.

Asexual Reproduction: Asexual reproduction of the new cultivar 'CF-MKR-EA1', by way of rooting stem cuttings, was first performed in March of 2023 at a commercial greenhouse near Miami, Florida. Through eight subsequent generations, the unique features of this cultivar have proven to be stable and true to type.

SUMMARY OF THE INVENTION

The cultivar 'CF-MKR-EA1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CF-MKR-EA1'. These characteristics in combination distinguish 'CF-MKR-EA1' as a new and distinct *Epipremnum* cultivar:

1. *Epipremnum* 'CF-MKR-EA1' exhibits trailing and vining growth habit with glossy cordate foliage; and
2. *Epipremnum* 'CF-MKR-EA1' exhibits juvenile foliage with a bright yellow general coloration; and
3. *Epipremnum* 'CF-MKR-EA1' exhibits juvenile foliage that becomes progressively mottled with yellow-green as it matures; and
4. *Epipremnum* 'CF-MKR-EA1' exhibits dark green mature foliage.

BOTANICAL DESCRIPTION OF THE PLANT

Figure 1:
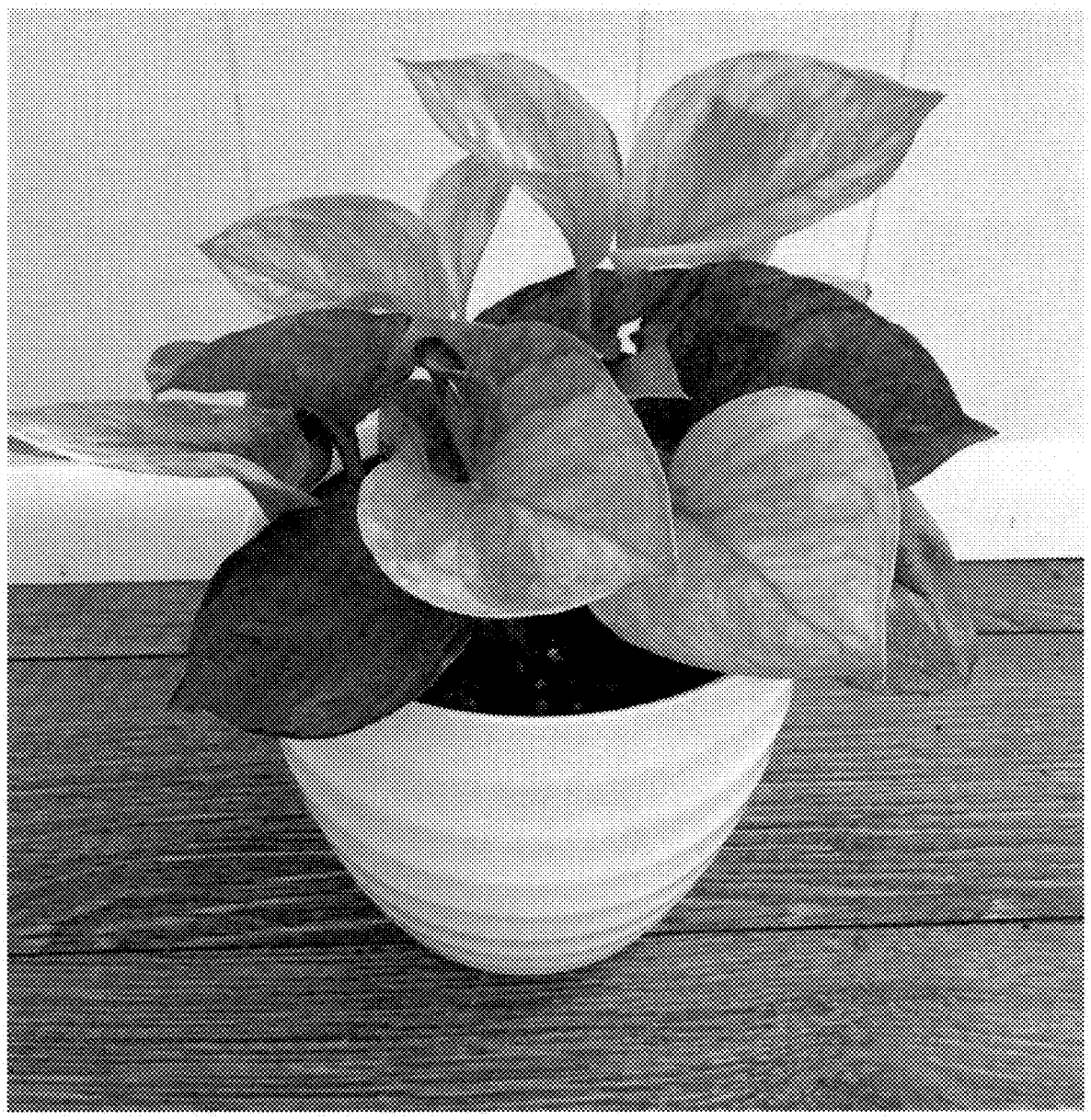
FIG. 1 illustrates, as nearly true as it is reasonably possible to make the same in color photographs of this type, an exemplary 4.5-month-old 'CF-MKR-EA1' plant in a 15 cm nursery pot, grown in a greenhouse in Miami, Florida.
Figure 2:
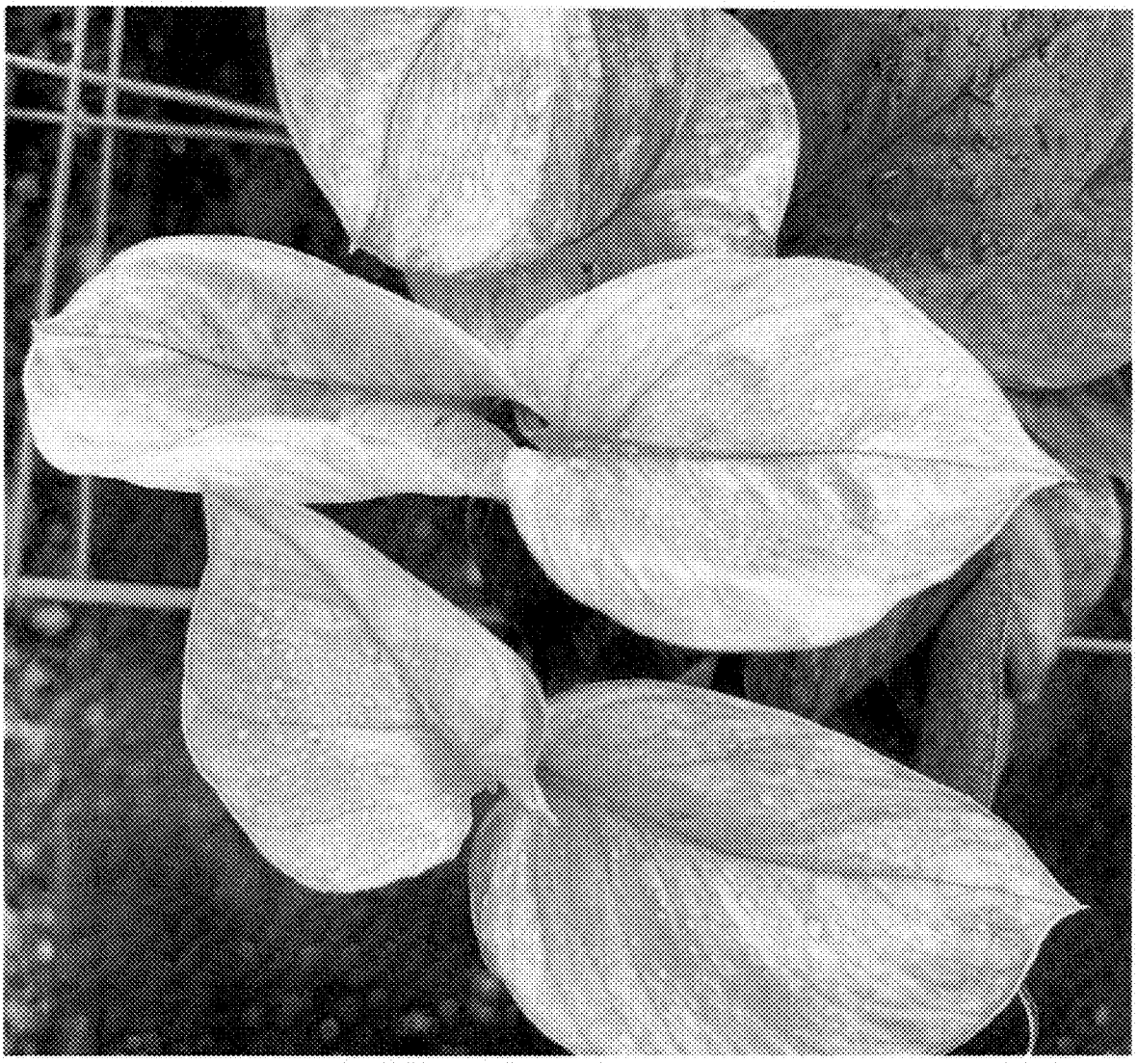
FIG. 2 illustrates, as nearly true as it is reasonably possible to make the same in color photographs of this type, the juvenile foliage of 'CF-MKR-EA1'.
Figure 3:
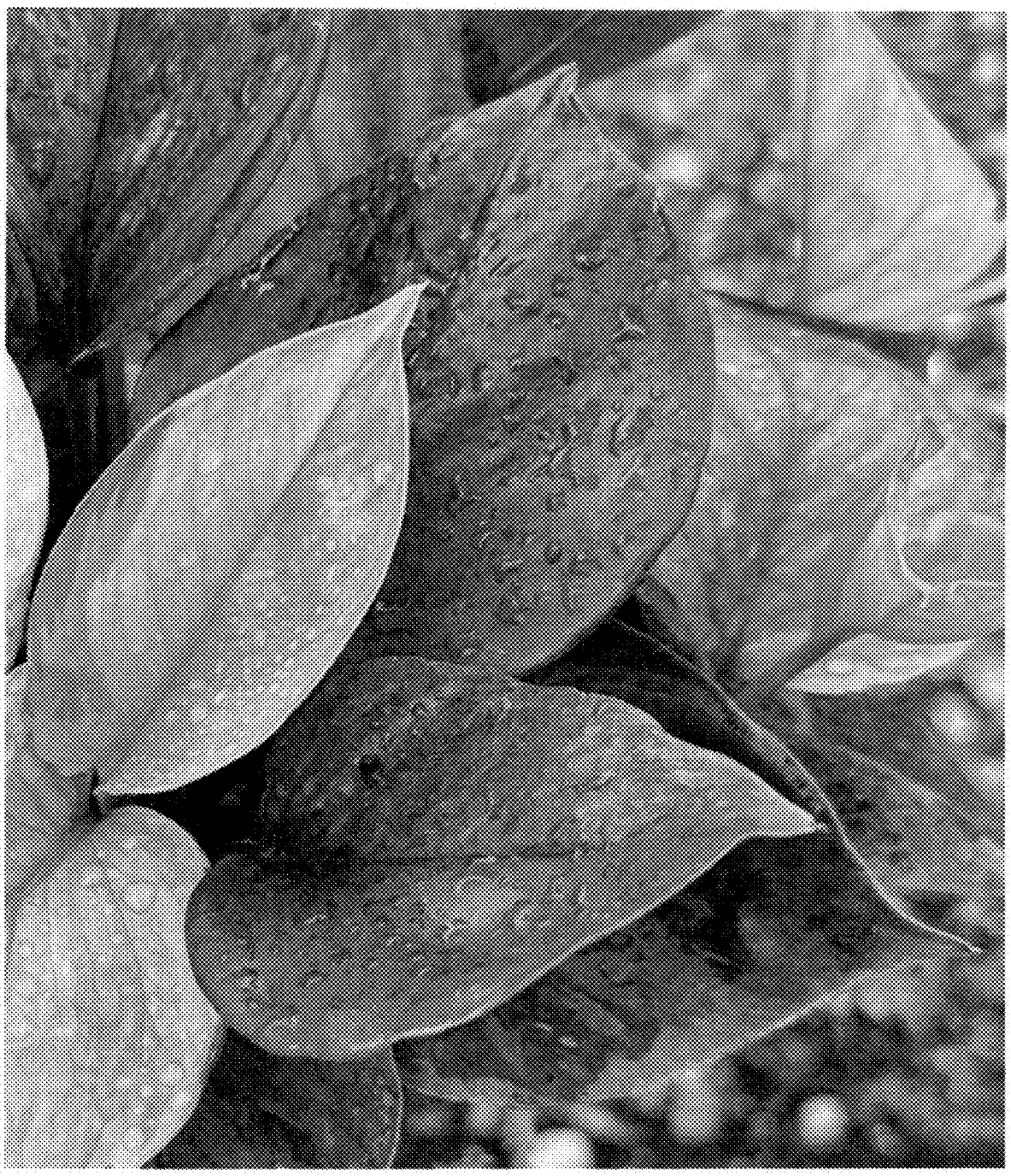
FIG. 3 illustrates, as nearly true as it is reasonably possible to make the same in color photographs of this type, the mature foliage of 'CF-MKR-EA1', partially obscured by juvenile foliage.

The following observations and measurements, made in November of 2023, describe a 9-month-old 'CF-MKR-EA1' plant. The plant was grown from a single unrooted cutting, in 15 cm nursery containers, at a commercial greenhouse near Miami, Florida. The plant was produced using conventional greenhouse production protocols for *Epipremnum* sp. which entailed growing plants under 80 percent shade, regularly watering with overhead irrigation, and fertilizing with a 180-day slow-release granular fertilizer. No chemical pest measures or photoperiodic treatments were utilized during production.

Those skilled in the art will appreciate that certain characteristics will vary with older or, conversely, with younger plants. 'CF-MKR-EA1' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, second edition.

A botanical description of 'CF-MKR-EA1' and a comparison with the parent, which is also the most similar commercial variety of *Epipremnum aureum* known to the inventor, are provided below.

Plant description:

*Growth habit*.—Evergreen trailing and vining perennial.

*Average height from base to top of foliage*.—11 cm, as observed.

*Average width*.—41.0 cm, as observed.

*Growth rate*.—Fast growing.

*Plant vigor*.—Vigorous.

*Propagation method*.—Softwood stem cuttings; rooting is initiated in approximately 14 to 21 days, when grown in a greenhouse with an ambient average temperature of 26 to 32 degrees Celsius, respectively.

*Time to produce a finished plant*.—Approximately 14 to 16 weeks are required to produce a fully rooted and marketable 14 cm plant from an unrooted cutting, when grown under greenhouse conditions.

*Disease and pest resistance or susceptibility*.—Plants have not been observed to be susceptible or resistant to pathogens and pests common to *Epipremnum* sp.

*Environmental tolerances*.—Adapt to at least USDA Zones 10 and 12; high tolerance to rain; high tolerance to wind; low tolerance to drought.

Root system:

*General*.—*Epipremnum* sp. has the propensity to produce both subterranean and aerial roots.

*Branching*.—Freely branched.

*Density*.—Moderately dense.

*Distribution*.—Subterranean roots are shallow to moderately deep.

*Texture*.—Fleshy; smooth; lacking root hairs.

Stem:

*Aspect*.—Terete; striate.

*Length of stems*.—16.5 cm, as observed.

*Diameter of stems*.—0.7 cm at the widest point.

*Internode length*.—3.7 cm.

*Attitude*.—Prostrate; weeping, when grown in a hanging basket.

*Strength*.—Weak.

*Texture and luster*.—Glabrous and glossy.

*Color, juvenile*.—Yellow-green, nearest to RHS 144B.

*Color, mature*.—Yellow-green, nearest to RHS 144A yet darker.

Foliage:

*Arrangement*.—Alternate.

*Division*.—Simple.

*Attachment*.—Petiolate.

*Abundance of foliage*.—Very abundant.

*Lamina*.—Dimensions — 10.5 cm long and 8.6 cm wide, on average. Shape — Broadly cordate. Aspect — Varying from convex to concave or wavy; margins occasionally involute or revolute. Apex — Acuminate. Base — Cordate. Margin — Entire; coarsely undulate. Pubescence, texture and luster of adaxial surface — Glabrous, smooth, and glossy. Pubescence, texture and luster of abaxial surface — Glabrous, smooth, and very slightly glossy. Color — Juvenile foliage, adaxial surface — Green-yellow, nearest to RHS 154B; occasionally blotched or broadly and irregularly margined with yellow-green, nearest to a combination of RHS 144B and 144C. As foliage matures, it becomes progressively mottled with yellow-green, nearest to RHS 144C. Juvenile foliage, abaxial surface — Green-yellow, nearest to RHS 154C; occasionally blotched or broadly and irregularly margined with yellow-green, nearest to RHS 144C. As foliage matures, it becomes progressively mottled with yellow-green, nearest to RHS 144C. Mature foliage, adaxial surface — Green, nearest to RHS 137A yet darker. Mature foliage, abaxial surface — Green, RHS 138B. Venation — Pattern — Pinnate. Juvenile venation color, adaxial surface — Yellow-green, RHS 144B. Juvenile venation color, abaxial surface — Main veins and lateral veins are yellow-green, nearest to RHS 145B. Mature venation color, adaxial surface — Indistinguishable from the surrounding foliage. Mature venation color, abaxial surface — Main veins are yellow-green, nearest to RHS 145C. Lateral veins are indistinguishable from the surrounding foliage.

*Petiole*.—Aspect — Terete. Length — 7.0 cm. Width — 0.5 cm. Texture — Smooth and glabrous. Luster — Slightly glossy. Strength — Moderately strong. Color, juvenile petioles — Yellow-green, RHS 145B. Color, mature petioles — Yellow-green, nearest to RHS 144A yet darker.

*Stipules*.—General — Two long and narrow stipules are fused to the petiole; stipules desiccate as foliage matures and will eventually senesce with age. Length — 5.5 cm. Width — 0.45 cm at the base. Texture — Smooth and glabrous. Luster — Slightly glossy. Color, juvenile stipules — Yellow-green, nearest to RHS 145D. Color, mature stipules — Brown, nearest to RHS 200C.

Inflorescence: To date, no flowering has been observed.

Bud: To date, no flowering has been observed.

Flower: To date, no flowering has been observed.

Reproductive organs: To date, no flowering has been observed.

Seed and fruit: To date, no flowering has been observed.

COMPARISON WITH THE PARENT PLANT

Plants of the new cultivar 'CF-MKR-EA1' differ from the parent, *Epipremnum aureum* 'Lemon Meringue' plants (U.S. Pat. No. 34,521) which is also the most similar commercial variety known to the inventor, by the characteristics described in Table 1.

TABLE 1

| Characteristic | 'CF-MKR-EA1' | 'Lemon Meringue' |
|---|---|---|
| Presence of foliage variegation. | Not present. | Present. |
| General coloration of the juvenile foliage. | Green-yellow, nearest to RHS 154B, generally appearing as yellow. | Centered green, and broadly and irregularly margined yellow. |
| General coloration of the mature foliage. | Dark green. | Centered dark green, and broadly and irregularly margined with either yellow or light yellow-green with yellow mottling. |

That which is claimed is:

1. A new and distinct *Epipremnum aureum* plant named 'CF-MKR-EA1', substantially as described and illustrated herein.

* * * * *